United States Patent [19]

Choucair et al.

[11] Patent Number: 5,267,566
[45] Date of Patent: Dec. 7, 1993

[54] APPARATUS AND METHOD FOR BLOOD PRESSURE MONITORING

[76] Inventors: Maged Choucair, 4001 W. McNichols, Detroit, Mich. 48221; Eugene Kordyban, 19154 Charest, Detroit, Mich. 48234

[21] Appl. No.: 957,455

[22] Filed: Oct. 6, 1992

Related U.S. Application Data

[63] Continuation of Ser. No. 666,024, Mar. 7, 1991, abandoned.

[51] Int. Cl.⁵ .................................................. A61B 5/02
[52] U.S. Cl. ...................................... 128/675; 128/680
[58] Field of Search ................. 128/632, 672, 675, 680, 128/687, 688, 689, 774; 338/4

[56] References Cited

U.S. PATENT DOCUMENTS

| | | | |
|---|---|---|---|
| 3,149,628 | 9/1964 | Bolie | 128/680 |
| 3,154,066 | 10/1964 | Grindheim et al. | 128/687 |
| 3,748,623 | 7/1973 | Millar | 338/4 |
| 4,030,484 | 6/1977 | Kuska et al. | 128/672 |
| 4,213,348 | 7/1980 | Reinertson et al. | 128/774 X |
| 4,311,980 | 1/1982 | Prudenziati | 338/4 |
| 4,332,258 | 6/1982 | Arai et al. | 128/687 X |
| 4,334,544 | 6/1982 | Hill et al. | 128/687 |
| 4,685,464 | 8/1987 | Goldberger et al. | 128/687 X |
| 4,915,116 | 4/1990 | Hasebe et al. | 128/687 X |
| 4,971,062 | 11/1990 | Hasebe et al. | 128/687 X |
| 5,036,857 | 8/1991 | Sennlow et al. | 128/680 X |
| 5,054,495 | 10/1991 | Uemura et al. | 128/680 |
| 5,065,749 | 11/1991 | Hasebe et al. | 128/687 X |

FOREIGN PATENT DOCUMENTS

| | | | |
|---|---|---|---|
| 3516338 | 11/1986 | Fed. Rep. of Germany | 128/675 |
| 2180944 | 4/1987 | United Kingdom | 128/672 |

*Primary Examiner*—Randall L. Green
*Assistant Examiner*—Mary Beth O. Jones
*Attorney, Agent, or Firm*—Barnes, Kisselle, Raisch, Choate, Whittemoe & Hulbert

[57] ABSTRACT

A method and apparatus for monitoring blood pressure by a transducer engaging a flexible part of a body near capillaries and remote from an artery. The transducer provides an electrical signal when actuated by blood pressure pulses or changes in the capillaries. The transducer is releasably secured to the body by a gripping means preferably in the form of a clothespin. The transducer includes a strip with two strain gages disposed one on each respective side of the strip such that the blood pressure pulses flex the strip causing a change in the electrical resistance of the gages. Preferably, the apparatus has electronic circuitry to convert the change in the resistance of the strain gages to a voltage signal indicative of blood pressure and devices for recording and displaying blood pressure.

11 Claims, 2 Drawing Sheets

APPARATUS AND METHOD FOR BLOOD PRESSURE MONITORING

This is a continuation of copending application Ser. No. 07/666,024, filed on Mar. 7, 1991, now abandoned.

FIELD OF THE INVENTION

This invention relates to blood pressure monitoring devices and, more particularly, to a device which is noninvasive and which is not affected by movement of the skin.

BACKGROUND OF THE INVENTION

Blood pressure varies with each heart beat, and varies between high and low levels, most commonly known as systolic and diastolic pressures. The monitoring of pressure that blood exerts on the walls of arteries is the most popular prior art method used to determine blood pressure. Pressures are commonly obtained by using a stethoscope and a sphygmomanometer, in the method known as the cuff method. It is not convenient to monitor pressure and/or the change in pressure over a long period of time by use of the sphygmomanometer because it is labor intensive as it entails measuring the blood pressure by comparing the pressure in the main artery of the arm with the pressure in an inflatable cuff wrapped around the arm. The sphygmomanometer restricts muscle movement, is uncomfortable and chafes the skin.

Prior art devices for automatically monitoring blood pressure include U.S. Pat. No. 2,549,049 which describes a diaphragm type blood pressure gage which has a flexible membrane sensor in contact with the skin directly over an artery. The membrane is equipped with a monitor which generates an output related to blood pressure. This method basically requires monitoring a change in the position of the membrane by arterial distension due to variation of blood pressure. A problem arises because it is difficult to accurately position the membrane over the artery, calibrate the device, and account for the effect of tissue elasticity, density and/or skin displacement. In addition, certain drugs reduce blood pressure while at the same time increasing arterial distention.

U.S. Pat. No. 3,704,708, describes a similar device used to measure the displacement of a membrane sensor which is secured in a housing. In use, the membrane is secured to a skeletal portion of the head. The device engages a bony grooved region which encompasses a vascular duct. The housing defines a laterally extending open channel defined by ridged or shoulder portions. The shoulders fit over a complementary vascular duct and engage the bony region about the duct, thereby holding the membrane within a channel and pressing against the duct.

It has been found that it is very difficult to keep a membrane sensor directly over an artery since any body or tissue motion may relatively move the sensor sufficiently to prevent a correct reading from being obtained. Further, there are indications that the artery itself attempts to move when compressed. Once the sensor is shifted from its original position the readings will be affected. In addition, the elasticity of the tissue will vary depending on the proximity of the sensor to the artery and also affect the accuracy of the readings.

SUMMARY OF THE INVENTION

A method and apparatus for monitoring blood pressure by a transducer engaging a flexible part of a body near arterioles and capillaries and remote from an artery. The transducer provides an electrical signal when actuated by blood pressure pulses or changes in the capillaries and arterioles. The transducer is releasably secured to the body by a gripping means preferably in the form of a clothespin. The transducer includes a strip with two strain gages disposed one on each respective side of the strip such that the blood pressure pulses flex the strip causing a change in the electrical resistance of the gages. Preferably, the apparatus has electronic circuitry to convert the change in the resistance of the strain gages to a voltage signal and devices for recording and displaying blood pressure.

The apparatus may be used to monitor blood pressure and/or relative changes in blood pressure. In use the transducer is placed in engagement with a flexible part of the body which is remote from an artery. The change in the electrical resistance of the strain gages is monitored. The change in resistance is then converted to a voltage signal which corresponds to changes in blood pressure. By this method, relative changes in blood pressure are monitored by way of relative changes in the voltage signal.

The device may also be used to monitor the numerical value of the blood pressure by calibrating the voltage signal. Calibration for each patient is accomplished by comparing the numerical value of the voltage signal to the numerical value obtained from a standard sphygmomanometer. Thereafter changes in voltage may be directly converted to the numerical value of the blood pressure.

Preferably, if the device is to be attached to a patient for a long period of time, it may be desirable to periodically check it against a sphygmomanometer and recalibrate it as necessary. An automated system of calibration checks may include the use of a computer therefore not requiring intervention by a human operator.

Objects, features and advantages of this invention are to provide a method and apparatus which are insensitive to bodily motions which are not associated with blood pressure, an apparatus which may be placed in locations such as an ear lobe which are not normally mobile in the course of human activity and where interference from motion will be minimized, transducers which are not directly in contact with the body but are in indirect contact therewith and move in one direction only with the change in blood pressure, can continuously monitor blood pressure, is easy to use, of relatively simple design and of economical manufacture and assembly.

BRIEF DESCRIPTION OF THE DRAWINGS

These and other objects, features and advantages of this invention will be apparent from the following detailed description, appended claims and accompanying drawings in which:

DETAILED DESCRIPTION OF PREFERRED EMBODIMENTS

Figure 1:
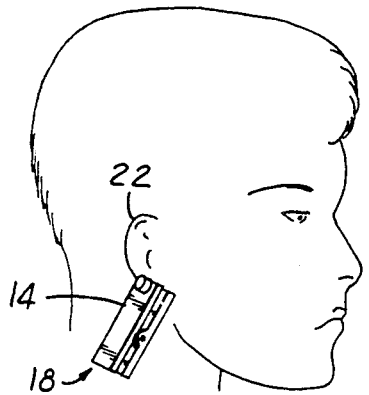
FIG. 1 is a perspective view of a sensor of the invention in engagement with an ear lobe.
Figure 2:
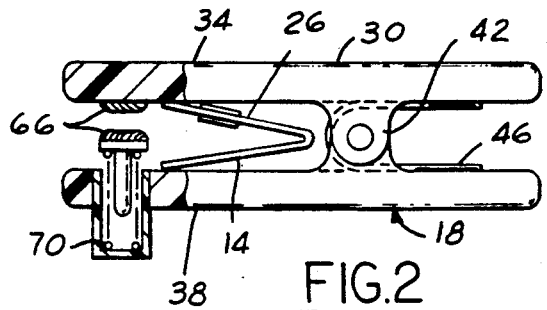
FIG. 2 is a side view of the sensor of FIG. 1, partially in section.
Figure 3:
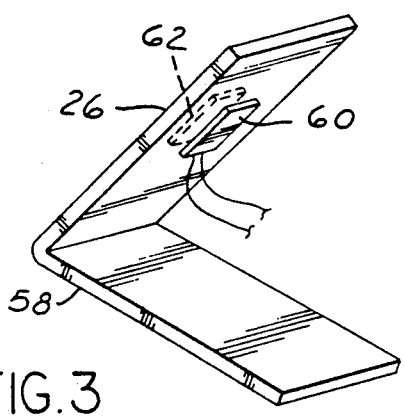
FIG. 3 is a perspective view of a transducer of the sensor of FIG. 1.
Figure 4:
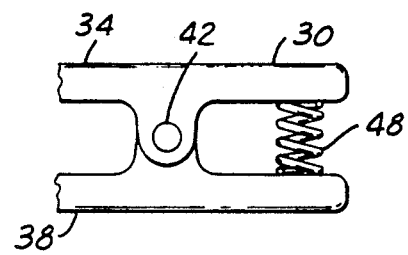
FIG. 4 is a fragmentary side view of another embodiment of a sensor.
Figure 5:
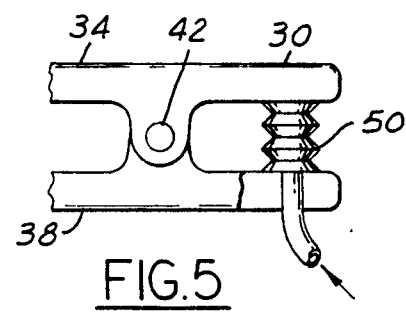
FIG. 5 is a fragmentary side view of another embodiment of a sensor.

FIG. 1 illustrates a human head 10 with a preferred sensor 14 of an apparatus 18 of the invention engaging an ear lobe 22. As shown in FIGS. 2 and 3, the sensor 14 has a transducer 26 held by gripping means 30 for abutting engagement with a flexible part of a body. Preferably, the gripping means 30 permits motion in one direction only and comprises opposed arms 34, 38 connected by a hinge 42 and biased together by biasing means. Preferably, the gripping means 30 is in the form of a clothespin but with a closing force which is considerably less. The gripping means 30 should be rigid but preferably of light weight material such as plastic. Biasing means may include a torsion spring 46, as shown in FIG. 2. Alternatively, the biasing means may be a coiled spring 48, (FIG. 4), or fluid actuated bellows 50, (FIG. 5).

In order to comfortably engage the apparatus 18 to portions of the body of varying dimensions, the gripping means 30 is equipped with soft pads 66 where the apparatus 18 engages body flesh, such as the ear lobe 22, (FIG. 1). The pads 66 are made of a flexible material such as foamed plastic and their purpose is to minimize the discomfort of engagement and provide a substantially constant area of engagement with the body. Preferably, one of the pads 66 is fixed to one arm of the gripping means 30 and the other pad is carried by the other arm and yieldably fixed by spring 70.

The apparatus can be applied to many parts of the body having capillaries and arterioles remote from an artery, for example, the nose, toes, fingers and ear lobes.

Figure 8:
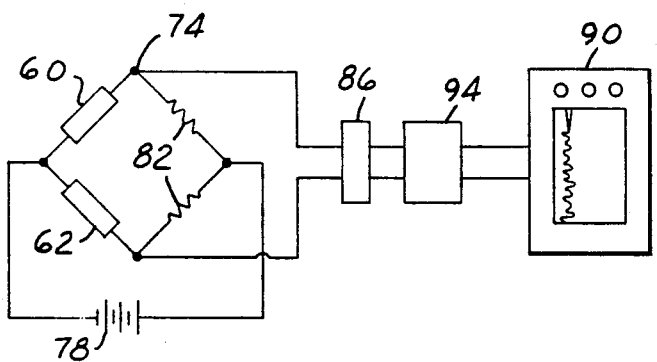
FIG. 8 is a schematic diagram which includes a circuit of an apparatus of FIG. 1 embodying this invention.
Figure 7:
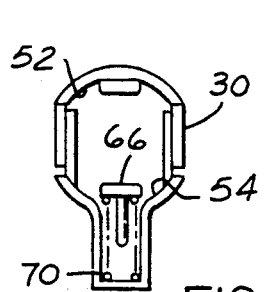
FIG. 7 is a sectional view of the sensor taken generally on line 7—7 of FIG. 6.
Figure 6:
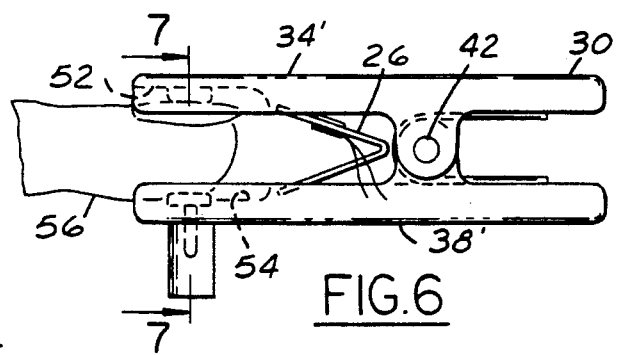
FIG. 6 is a side view of another embodiment of a sensor engaged to a finger tip.
Figure 9:
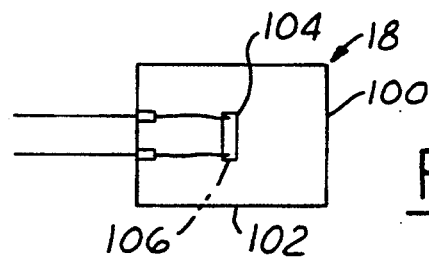
FIG. 9 is a top view of another embodiment of a sensor of the invention.
Figure 10:
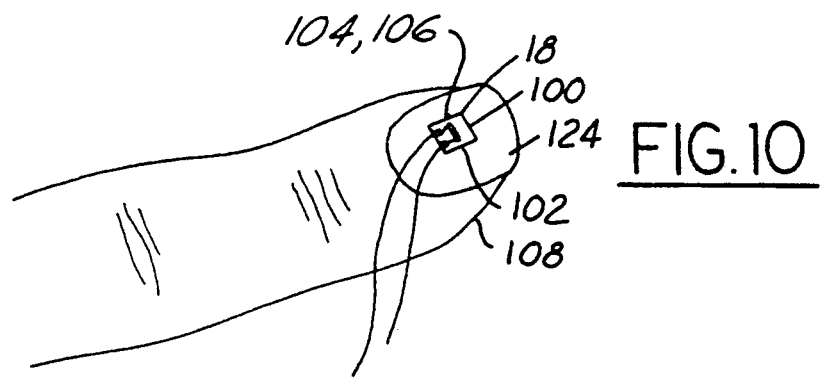
FIG. 10 is a perspective view of the sensor of FIG. 9 in engagement with a fingernail.
Figure 11:
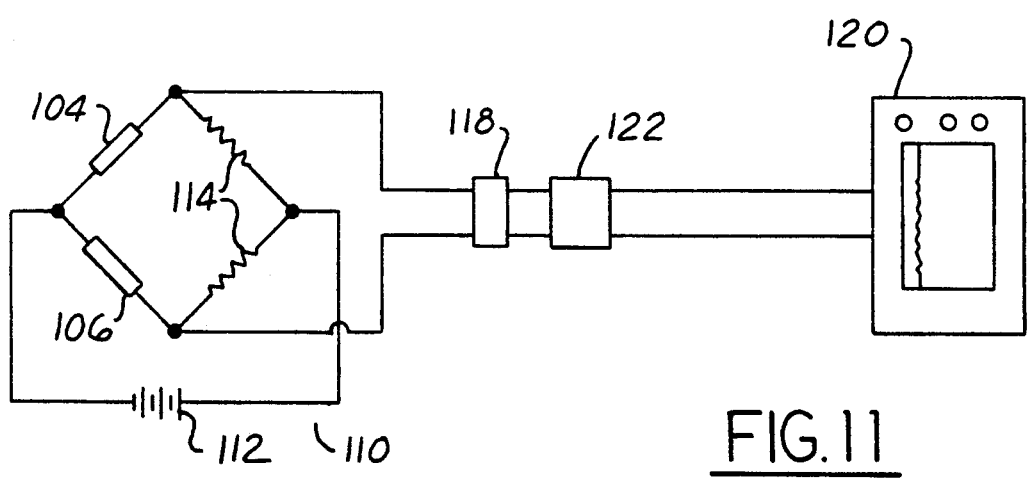
FIG. 11 is a schematic diagram which includes a circuit of an apparatus of FIG. 9 embodying this invention.

If it is desired to attach the apparatus 18 to a finger, preferably, as shown in FIGS. 6, 7 and 8, the opposed arms 34 and 38 each have semi-circular recesses or end portions 52 and 54 constructed and arranged to receive a fingertip 56.

In use, the opposed arms 34, 38 of gripping means 30 are moved by blood pressure changes produced by capillaries, for example, of the ear lobe 22. This movement is sensed by a transducer 26. The transducer 26 includes a strip 58 with at least one, and preferably two strain gages 60 and 62 disposed one on each respective side of the strip 58. In this arrangement, blood pressure changes which move arms 34, 38 cause flexing or the strip 58 which causes a change in the electrical resistance of the gages 60 and 62 (FIGS. 2 and 3). This change in resistance can be used to produce an electric signal indicative of a change in blood pressure.

In order to convert the changes in the resistance of the strain gages 60 and 62 to a voltage signal, preferably, the apparatus 18 includes appropriate circuitry. As shown in FIG. 8, the strain gages 60 and 62 constitute one half of a Wheatstone bridge 74. The preferred electrical circuit has the two strain gages 60 and 62, a power supply 78, and resistors 82 which provide an output signal to a filter 86 which removes extraneous frequencies and provides an output signal to a chart or strip recorder 90.

Preferably, the output of the bridge 74 is in the millivolt range and may be amplified by an amplifier 94, if desired. Since the human body appears to be a source of various higher frequency signals which tend to obscure the blood pressure curve, desirably, the filter 86 passes through signals of a frequency below about 30 herz and preferably below about 20 herz. Preferably, the signal is amplified 100 times and consists of all signals below about 20 hertz.

To obtain a continuous blood pressure curve, the amplified and filtered signal may be supplied to the recorder 90, which may be a chart paper recorder, oscilloscope or digital display device. If desired, the signal also may be used to power an alarm which is activated once preset values of blood pressure are reached.

In use, the transducer 26 is placed in abutting engagement with a flexible portion of a body, remote from an artery and near capillaries and arterioles, and changes in electrical resistance of the gages 60 and 62 are monitored and converted to a voltage signal. Relative changes in the voltage signal are monitored over time. The amplitude of the signal is then adjusted so the top of the curve shows the systolic blood pressure and the bottom of the curve shows the diastolic value of the blood pressure. The transducer 26 should be checked periodically thereafter to assure its continued proper calibration.

In another embodiment, an apparatus 18 of the invention has a transducer 100 which includes a strip 102 preferably of a thin polyimide film. Two semi-conductor gages 104, 106 are adhered, preferably by being glued, to respective sides of the strip 102. The strip 102 is adapted to be disposed over a slightly flexible portion of a body, such as a fingernail 124 of a finger 108, and adjacent capillaries (not shown). Preferably, the strip 102 is glued to the surface of a fingernail 124 which advantageously provides stable readings as the fingernail 124 may remain stable and not be affected by other body motions. Thus, it would be possible to study blood pressure behavior during various forms of physical exercise. In this arrangement, blood pressure changes cause flexing of the strip 102 which causes a change in the electrical resistance of the gages 104, 106. This change in resistance can be used to produce an electrical signal indicative of a change in blood pressure.

In order to convert the changes in the resistance of the strain gages 104, 106 to a voltage signal, preferably, the strain gages 104, 106 constitute one-half of a Wheatstone bridge 110, as described above. Preferably, the electrical circuit also has a power supply 112 and resistors 114 which along with the gages 104, 106 provides an output signal to a filter 118 which removes extraneous frequencies and provides an output signal to a chart or strip recorder 120, as described above. An amplifier 122 may be used if desired.

Preferably, at least the Wheatstone bridge 110 portion of the circuit is included with the strain gages 104, 106 on the strip 102.

Preferably, the semi-conductor gages 104, 106 are of a material which is compatible with the thermal characteristics of the preferred polyimide film strip 102 so as to produce a stable output.

The device provides the advantage that the semiconductor strain gages 104, 106 are more sensitive than typical metallic strain gages.

The apparatus 18 does not provide a numerical value for blood pressure directly as its output signal depends in part on the clamping or engagement pressure and the elasticity of the tissue which is expected to vary from person to person. Thus, a calibration is performed each time the apparatus 18 is engaged with a human body. The calibration may be accomplished by comparing the numerical values of the output voltage signal to the numerical values of blood pressure obtained with a standard sphygmomanometer.

For transducers 26, 100 positioned on the finger, the calibration procedure must be modified, since pressure in the cuff used with the sphygmomanometer will stop the blood flow to the finger and the signal will disappear. Thus the apparatus 18 of FIG. 6 was tested using Korotkoff sounds detected with a sound meter. The Korotkoff sounds are distinct sounds produced by the blood flow which appears during the release of the cuff pressure when systolic pressure is reached and disappears with the attainment of diastolic pressure. The output signal of the apparatus 18 at peak blood pressure (maximum amplitude) corresponded to the distinct Korotkoff sound observed at the time peak flow occurred. Similarly, the apparatus 18 produced a low blood pressure signal when the Korotkoff sound corresponding to low pressure occurred. Thus, Korotkoff sounds verified the occurrence of peak and low blood flow monitored by the apparatus 18, although the amplitude was not compared to a standard due to the limitation of the Korotkoff sound test. The comparison to Korotkoff sounds showed that the first appearance of the blood pressure peaks corresponded accurately to the initiation of Korotkoff sounds, while their disappearance corresponded to the end of the signal growth. Thus, the systolic and diastolic pressure can be determined and the relative peak and valley of amplitude may be set.

If it is desired to monitor the value of blood pressure over a period of time, the apparatus 18 may be used by placing the transducer 26 or 100 in abutting engagement with a flexible portion of a body remote from an artery, monitoring the changes in electrical resistance, converting the changes to an electric signal and then calibrating the signal by comparing the numerical values of the signal to the numerical values obtained from a standard sphygmomanometer. Thereafter, the electric signal may be directly converted to a blood pressure value. Preferably, periodic calibration checks will be made.

Presently automatic sphygmomanometers are available which periodically apply the pressure to the cuff and make and record blood pressure readings. If the apparatus 18 is to be attached to a patient for a long period of time, and it is desired to check it against a sphygmomanometer periodically, it would be advantageous to use an automatic sphygmomanometer which operates periodically to check and if needed recalibrate, the reading of the apparatus 18 from time to time without the need of an operator. This can be accomplished by a simple computer program.

The apparatus 18 was tested in a clinical setting where it produced stable and reliable results. The blood pressure curve was accurate as evidenced by clearly visible dichrotic notch portions of the arterial pulse. In addition, the curve produced by the apparatus 18 clearly showed a change in blood pressure when a Valsalva Maneuver was performed.

Key advantages of the apparatus 18 are that it may be used to monitor pressure without interference by an artery or vascular duct, as the sensor may be placed in areas where interference from such ducts and arteries will not occur. The apparatus 18 is not affected by skin movement relative to the sensor because it responds to movement in one direction only, that is, in a direction perpendicular to the surface of engagement. The apparatus 18 provides continuous monitoring of blood pressure without the use of an invasive probe and is convenient, economical and not affected by factors such as elasticity and compressability of tissue.

We claim:

1. A blood pressure sensing apparatus for monitoring blood pressure in a body having at least one of a capillary or arteriole and at least one artery comprising: a pair of generally opposed arms pivotally connected together at a point spaced from one end thereof, a pair of generally opposed pads carried by said arms adjacent said one end thereof and constructed and arranged to receive between then a flexible part of the body having therein at least one of a capillary or arteriole adjacent at least one of said pads and remote from the arteries of the body, means carried by said arms and yieldably biasing said pads into engagement with such flexible part of the body; a flexible strip spaced from said pads, having a generally U-shape configuration with a central portion having a return bend and a pair of spaced apart ends operably connected with said arms to flex the strip in response to changes in blood pressure in such at least one of a capillary or arteriole adjacent said at least one pad; and at least one strain gauge disposed on said strip between said return bend and one of said ends thereof and constructed and arranged to change its electrical resistance in response to flexing of said strip, whereby the electrical resistance changes in response to changes in blood pressure in such at least one of a capillary or arteriole adjacent said at least one pad, while at least minimizing response to any other movement caused by activities of the body.

2. The apparatus of claim 1 wherein said means yieldably biasing said pads into engagement with such flexible part of the body comprises a spring.

3. The apparatus of claim 1 wherein said means yieldably biasing said pads into engagement with such flexible part of the body comprises a fluid actuated bellows.

4. The apparatus of claim 1 wherein said arms each have adjacent said one end thereof a generally semi-circular portion constructed and arranged to engage a digit.

5. The apparatus of claim 1 wherein said at least one strain gauge comprises two strain gauges disposed in generally opposed relation on opposite sides of said strip between said return bend and one of said ends thereof.

6. The apparatus of claim 1 wherein said at least one strain gauge is a semi-conductor strain gauge.

7. The apparatus of claim 1 which also comprises an electric circuit constructed and arranged to convert the change in the resistance of said at least one strain gauge to an electric signal indicative of blood pressure, said electric circuit having an electric signal amplifier and a filter which inhibits a signal with a frequency of greater than about 30 hertz.

8. The apparatus of claim 7 wherein at least a portion of said electric circuit is printed on at least one side of said flexible strip.

9. The apparatus of claim 7 wherein said electric circuit includes means for supplying an electric signal to a recorder for recording the values of blood pressure.

10. The apparatus of claim 7 wherein said electric circuit includes means for supplying a signal to a display device which visually displays the values of blood pressure.

11. The apparatus of claim 7 wherein said at least one strain gauge is a semi-conductor strain gauge.

* * * * *